(12) United States Patent
Kobayashi et al.

(10) Patent No.: US 11,540,795 B2
(45) Date of Patent: Jan. 3, 2023

(54) X-RAY DIAGNOSIS APPARATUS AND X-RAY DIAGNOSIS APPARATUS MANEUVERING DEVICE

(71) Applicant: CANON MEDICAL SYSTEMS CORPORATION, Otawara (JP)

(72) Inventors: Yoshiteru Kobayashi, Sakura (JP); Yosuke Kayukawa, Otawara (JP); Keisuke Sugawara, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 99 days.

(21) Appl. No.: 17/220,338

(22) Filed: Apr. 1, 2021

(65) Prior Publication Data

US 2021/0321965 A1 Oct. 21, 2021

(30) Foreign Application Priority Data

Apr. 16, 2020 (JP) .............................. JP2020-073711

(51) Int. Cl.
*A61B 6/00* (2006.01)
*A61B 6/04* (2006.01)

(52) U.S. Cl.
CPC ............ *A61B 6/467* (2013.01); *A61B 6/0407* (2013.01); *A61B 6/4458* (2013.01); *A61B 6/461* (2013.01); *A61B 6/54* (2013.01); *A61B 6/4464* (2013.01)

(58) Field of Classification Search
CPC ........ A61B 2017/00398; A61B 6/4208; A61B 5/704; A61B 6/46; A61B 8/4209; A61B 6/0487; A61B 6/04; A61B 6/566; A61B 6/4441; A61B 6/0407; A61B 6/548; A61B 6/4482; A61B 6/54; A61N 2005/1054; A61N 5/1069

See application file for complete search history.

(56) References Cited

FOREIGN PATENT DOCUMENTS

| JP | 8-275936 A | 10/1996 | |
|---|---|---|---|
| JP | 2016026534 A | * 2/2016 | ............... A61B 6/06 |
| JP | 2017-217143 A | 12/2017 | |
| JP | 2018-187124 A | 11/2018 | |

* cited by examiner

*Primary Examiner* — Don K Wong
(74) *Attorney, Agent, or Firm* — Oblon, McClelland, Maier & Neustadt, L.L.P.

(57) ABSTRACT

An X-ray diagnosis apparatus according to an embodiment includes: a table including a tabletop on which a patient is placed; an imaging unit including an X-ray tube to radiate X-rays onto the patient and an X-ray detector to detect X-rays; a maneuvering unit including a handle unit that is provided with contact sensors to detect contact made by an operator and is gripped by the operator and being configured to receive a maneuver to bring into operation the imaging unit and/or the table according to an operation of the handle unit; and a processing circuitry that judges whether the imaging unit and/or the table is to be brought into operation on the basis of detection results obtained by the contact sensors and that brings the imaging unit and/or the table into operation in accordance with a result of the judgment and the maneuver performed on the maneuvering unit.

14 Claims, 11 Drawing Sheets

X-RAY DIAGNOSIS APPARATUS AND X-RAY DIAGNOSIS APPARATUS MANEUVERING DEVICE

CROSS-REFERENCE TO RELATED APPLICATIONS

This application is based upon and claims the benefit of priority from Japanese Patent Application No. 2020-073711, filed on Apr. 16, 2020; the entire contents of which are incorporated herein by reference.

FIELD

Embodiments described herein related generally to an X-ray diagnosis apparatus and an X-ray diagnosis apparatus maneuvering device.

BACKGROUND

Conventionally, X-ray diagnosis apparatuses may be provided with a console to perform maneuvers on an arm supporting an X-ray tube, on a table, and in making front-and-back movements of an X-ray detector in relation to a Source Image Distance (hereinafter "SID"). For X-ray diagnosis apparatuses used on the circulatory system, such a console may be provided on a pedestal of a table, in a control room, or the like. As another example, for X-ray diagnosis apparatuses for an X-ray TV, such a console may be provided in a control room or the like. The abovementioned maneuvers can be performed by using a lever such as a joystick provided on the console. Joysticks include those using a single action method and those using a double action method. According to the single action method, it is possible to perform maneuvers only by tilting the joystick. According to the double action method, maneuvers are made possible by pressing a trigger switch provided on the joystick and tilting the joystick. The single action method and the double action method each have problems described below.
The single action method:
When an X-ray diagnosis apparatus with the single action method is used in an abnormal way, we cannot exclude the possibility that the joystick may be tilted and that the X-ray diagnosis apparatus may perform an operation not intended by the operator (e.g., the practitioner), when a body part of the practitioner or of a medical technologist in the examination room or the control room or an arm or a leg of the examined subject (hereinafter, "patient") inadvertently hits the joystick of the X-ray diagnosis apparatus used on the circulatory system or when a body part of a medical technologist or a medical doctor inadvertently hits the joystick of the X-ray diagnosis apparatus for an X-ray TV. For this reason, there is a problem where users who value safety may find that the single action method is insufficient in providing secure feelings.
The double action method:
Because the trigger switch and the joystick need to be maneuvered at the same time, maneuvering requires more effort, which may prevent smooth manipulation and imaging processes. For this reason, the double action method has a problem where operability is degraded.

DETAILED DESCRIPTION

Figure 1:
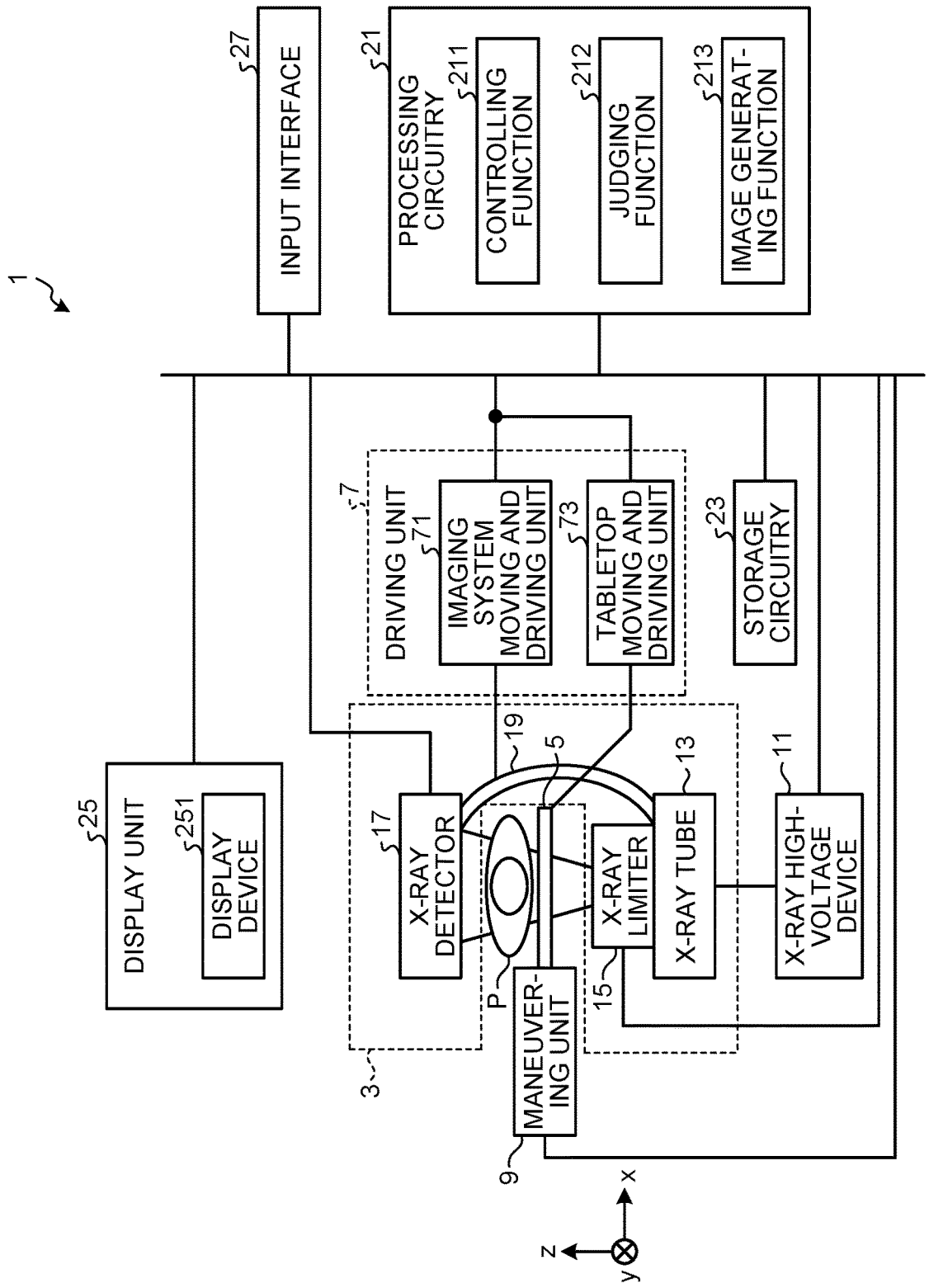
FIG. 1 is a diagram illustrating an exemplary configuration of an X-ray diagnosis apparatus according to an embodiment.

Exemplary embodiments of an X-ray diagnosis apparatus and an X-ray diagnosis apparatus maneuvering device will be explained in detail below, with reference to the accompanying drawings. In the following embodiments, some of the constituent elements referred to by using mutually the same reference characters are assumed to perform the same operations, and duplicate explanations thereof will be omitted as appropriate.

EMBODIMENTS

An X-ray diagnosis apparatus according to an embodiment of the present disclosure includes a table, an imaging unit, a maneuvering unit, and a processing circuitry. The table includes a tabletop on which a patient is placed. The imaging unit includes an X-ray tube configured to radiate X-rays onto the patient and an X-ray detector configured to detect X-rays. The maneuvering unit includes a handle unit provided with a plurality of contact sensors to detect contact made by an operator and gripped by the operator. The maneuvering unit is configured to receive a maneuver to bring into operation one or both of the imaging unit and the table according to an operation of the handle unit. The processing circuitry is configured to judge whether or not one or both of the imaging unit and the table is to be brought into operation on the basis of a plurality of detection results obtained by the plurality of contact sensors. The processing circuitry is configured to bring the one or both of the imaging unit and the table into operation in accordance with a result of the judgment and the maneuver performed on the maneuvering unit.

FIG. 1 is a diagram illustrating an exemplary configuration of an X-ray diagnosis apparatus 1 according to an embodiment of the present disclosure. In the embodiment described below, the X-ray diagnosis apparatus 1 will be explained which is used on the circulatory system and includes a supporting arm included in a holding device 19. The supporting arm is configured to support an X-ray tube 13 and an X-ray detector 17. The X-ray diagnosis apparatus 1 according to the present embodiment may be, for example, an X-ray TV apparatus for gastrointestinal diagnosis purposes. In that situation, the supporting arm is configured to support the X-ray tube 13, while the X-ray detector 17 is mounted on a table. In other words, the supporting arm included in the X-ray diagnosis apparatus 1 is configured to support the X-ray tube 13, with or without supporting the X-ray detector 17. The X-ray TV apparatus will be explained later as an application example.

The X-ray diagnosis apparatus 1 includes an imaging unit 3, a table 5, a driving unit 7, a maneuvering unit 9, an X-ray high-voltage device 11, a processing circuitry 21, a storage circuitry 23, a display unit 25, and an input interface 27. The imaging unit 3 includes the X-ray tube 13 configured to radiate X-rays onto the patient P and the X-ray detector 17 configured to detect X-rays, and further includes an X-ray limiter 15 and the holding device 19. In other words, the imaging unit 3 further include the supporting arm. The table 5 is provided with the maneuvering unit 9 used for bringing the imaging unit 3 and the table 5 into operation. The driving unit 7 configured to drive the imaging unit 3 and the table 5 includes an imaging system moving and driving unit 71 and a tabletop moving and driving unit 73.

The X-ray high-voltage device 11 includes electric circuits such as a transformer and a rectifier, as well as a high-voltage generating device and an X-ray controlling device. The high-voltage generating device has a function of generating high voltage to be applied to the X-ray tube 13 and a filament current to be supplied to the X-ray tube 13. The X-ray controlling device is configured to control output voltage in accordance with the X-rays radiated by the X-ray tube 13. The high-voltage generating device may be of a transformer type or of an inverter type. Alternatively, the X-ray high-voltage device 11 may be provided for the holding device 19.

The X-ray tube 13 is a vacuum tube configured to generate the X-rays by emitting thermo electrons from a negative pole (a filament) toward a positive pole (a target), with the application of the high voltage and the supply of the filament current from the X-ray high-voltage device 11. As a result of the thermo electrons colliding with the target, the X-rays are generated. Examples of the X-ray tube 13 include a rotating anode X-ray tube configured to generate the X-rays by emitting the thermo electrons onto a rotating anode (positive pole). Possible types of the X-ray tube 13 are not limited to the rotating anode type. It is possible to use an X-ray tube of any arbitrary type.

The X-ray limiter 15 is provided on the front face of an X-ray radiation window of the X-ray tube 13. The X-ray limiter 15 includes, for example, four limiting blades configured by using metal plates of lead or the like. The limiting blades are driven by a driving device (not illustrated) in accordance with a region of interest being input by an operator via the maneuvering unit 9 or the input interface 27. The X-ray limiter 15 is configured to adjust a region in which the X-rays are blocked so as to have an arbitrary size, by causing the driving device to slide the limiting blades. By using the adjusted limiting blades, the X-ray limiter 15 is configured to block the X-rays outside an opening region. Accordingly, the X-ray limiter 15 narrows down the X-rays generated by the X-ray tube 13 so as to be radiated onto the region of interest of the patient P.

The X-ray detector 17 is configured to detect the X-rays generated by the X-ray tube 13. For example, the X-ray detector 17 may be a Flat Panel Detector (hereinafter, "FPD"). The FPD includes a plurality of semiconductor detecting elements. Possible types of the semiconductor detecting elements include a direct conversion type by which X-rays are directly converted into electrical signals and an indirect conversion type by which X-rays are converted into light by using a fluorescent material so that the light is then converted into electrical signals. The FPD may be of either of these types. The electrical signals generated by the plurality of semiconductor detecting elements in conjunction with the X-rays becoming incident thereto are output to an analog-to-digital converter (hereinafter, "A/D converter") (not illustrated). The A/D converter is configured to convert the electrical signals into digital data. The A/D converter is configured to output the digital data to the processing circuitry 21. As the X-ray detector 17, an image intensifier may be used.

Figure 2:
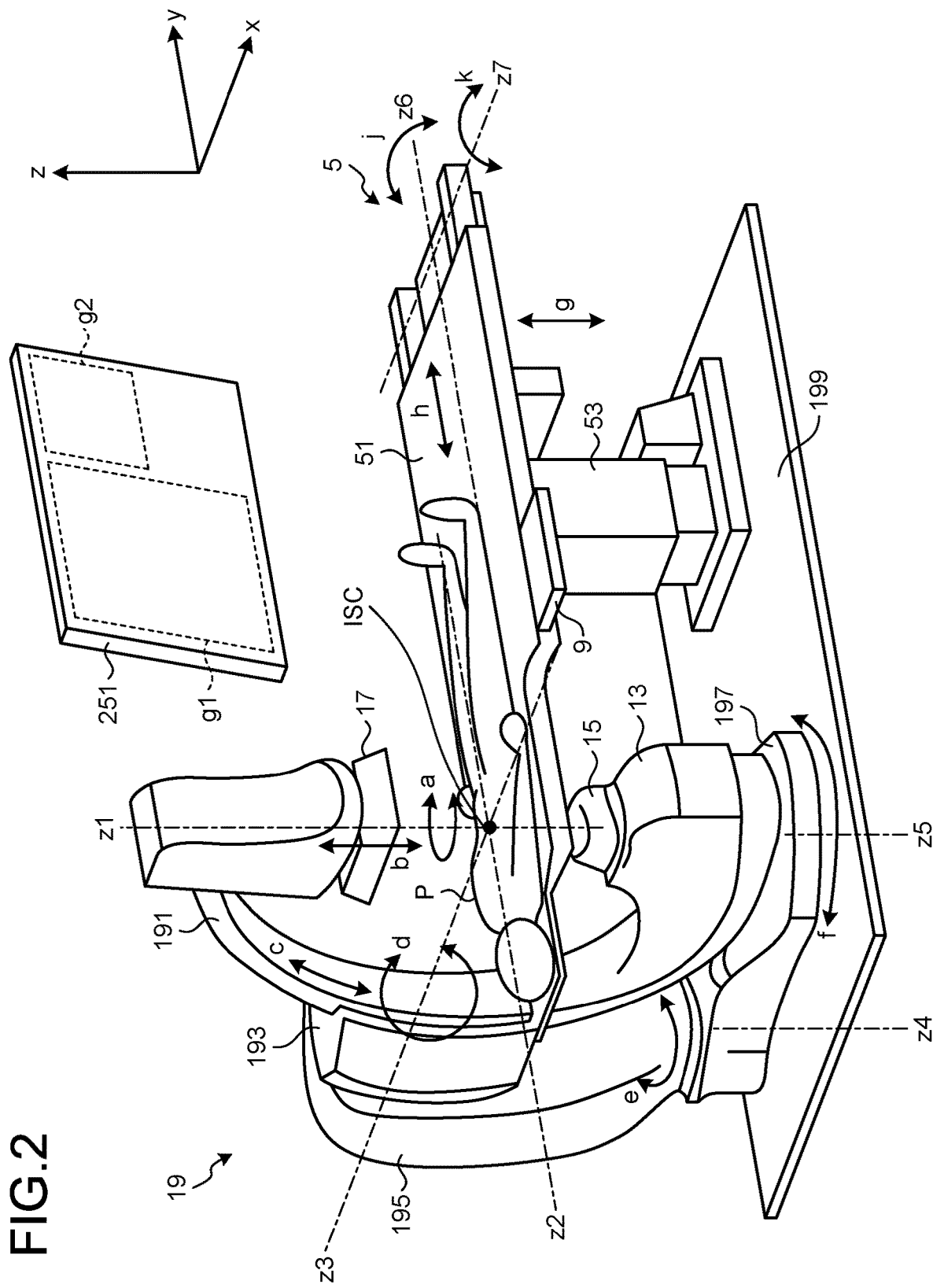
FIG. 2 is a drawing according to the embodiment illustrating examples of a floor-mounted holding device and a table.

Next, configurations of the floor-mounted holding device 19 and the table 5, as well as moving or rotating the units included in the holding device 19 and the table 5 will be explained. FIG. 2 is a drawing illustrating examples of the floor-mounted holding device 19 and the table 5 including a tabletop 51 on which the patient P is placed. The holding device 19 includes a C-arm 191 corresponding to the supporting arm, an arm holder 193, a stand 195, and a floor turning arm 197. The table 5 includes the tabletop 51 and a pedestal 53. In FIG. 2, to facilitate the description below, the longitudinal direction of the table 5 is expressed as a y-axis; the vertical direction is expressed as a z-axis; and the direction orthogonal to the y-axis and the z-axis is expressed as an x-axis.

The configurations of the holding device 19 and the table 5 illustrated in FIG. 2 are examples, and possible configurations are not limited to these examples. The supporting arm is not limited to the floor-mounted C-arm 191 illustrated in FIG. 2 and may be, for example, an Ω-shaped arm hung from the ceiling (hereinafter, "ceiling-mounted"). Further, the X-ray diagnosis apparatus 1 for the circulatory system may include the C-arm 191 and an Ω-shaped arm.

The driving unit 7 includes the imaging system moving and driving unit 71 and the tabletop moving and driving unit 73. Under control of a controlling function 211 of the processing circuitry 21, the imaging system moving and driving unit 71 is configured to drive the imaging unit 3 so as to move an imaging system such as the X-ray tube 13 and the X-ray detector 17 in a desired direction. For example, the imaging system moving and driving unit 71 is provided for the holding device 19 in correspondence with each of a plurality of supporting members (the C-arm 191, the arm holder 193, the stand 195, and the floor turning arm 197) that support a plurality of constituent elements to be moved. Under the control of the controlling function 211, the tabletop moving and driving unit 73 is configured to drive the table 5 so as to move the tabletop 51 in a desired direction. For example, the tabletop moving and driving unit 73 is provided for the table 5. The imaging system moving and driving unit 71 and the tabletop moving and driving unit 73 are each realized by using a motor, an actuator, or the like.

The C-arm 191 is configured to support the X-ray tube 13, the X-ray limiter 15, and the X-ray detector 17 on the two ends thereof. In other words, the X-ray tube 13 and the X-ray detector 17 are attached to the end parts of the C-arm 191 so as to oppose each other. The C-arm 191 is configured to rotatably support the X-ray limiter 15 and the X-ray detector 17, on a rotation axis $z1$ being a straight line connecting a focal point of the X-ray tube 13 where the X-rays are generated, to a center part of the X-ray detector 17. As a result of an operation of the imaging system moving and driving unit 71, the C-arm 191 rotates the X-ray limiter 15 and the X-ray detector 17 (hereinafter, "detector rotation") on the rotation axis $z1$ as indicated by the arrow a.

The C-arm 191 is configured to support the X-ray detector 17 in such a manner that a Source Image Distance (hereinafter, "SID"), which corresponds to the distance between the X-ray tube 13 and the X-ray detector 17, is variable. In other words, the C-arm 191 is configured to slidably support the X-ray detector 17 along the arrow b. As a result of an operation of the imaging system moving and driving unit 71, the C-arm 191 is configured to slide the X-ray detector 17 (hereinafter, "SID change") along the arrow b.

The arm holder 193 is configured to slidably support the C-arm 191 on a rotation axis $z2$ being the direction that goes through an isocenter ISC and is perpendicular to a plane including the C-arm 191. As a result of an operation of the imaging system moving and driving unit 71, the arm holder 193 is configured to slide the C-arm 191 (hereinafter, "C-arm sliding") on the rotation axis $z2$ as indicated by the arrow c. The arm holder 193 is supported by the stand 195.

The stand 195 is configured to rotatably support the arm holder 193 on a rotation axis $z3$ being the direction that goes through the isocenter ISC and is perpendicular to the rotation axis $z1$ and to the rotation axis $z2$. As a result of an operation of the imaging system moving and driving unit 71, the stand 195 rotates the arm holder 193 (hereinafter, "main rotation") on the rotation axis $z3$ as indicated by the arrow d. The stand 195 is supported by the floor turning arm 197.

The floor turning arm 197 is configured to rotatably support the stand 195 on a rotation axis $z4$ being the vertical direction going through a connection part between the stand 195 and the floor turning arm 197. As a result of an operation of the imaging system moving and driving unit 71, the floor turning arm 197 rotates the stand 195 (hereinafter, "columnar rotation") on the rotation axis $z4$ as indicated by the arrow e. The floor turning arm 197 is rotatably installed on a floor surface 199 on a rotation axis $z5$ being the perpendicular direction going through a connection part between the floor turning arm 197 and the floor surface 199. As a result of an operation of the imaging system moving and driving unit 71, the floor turning arm 197 rotates (hereinafter, "rotation on the floor") on the rotation axis $z5$ as indicated by the arrow f.

Figure 3:
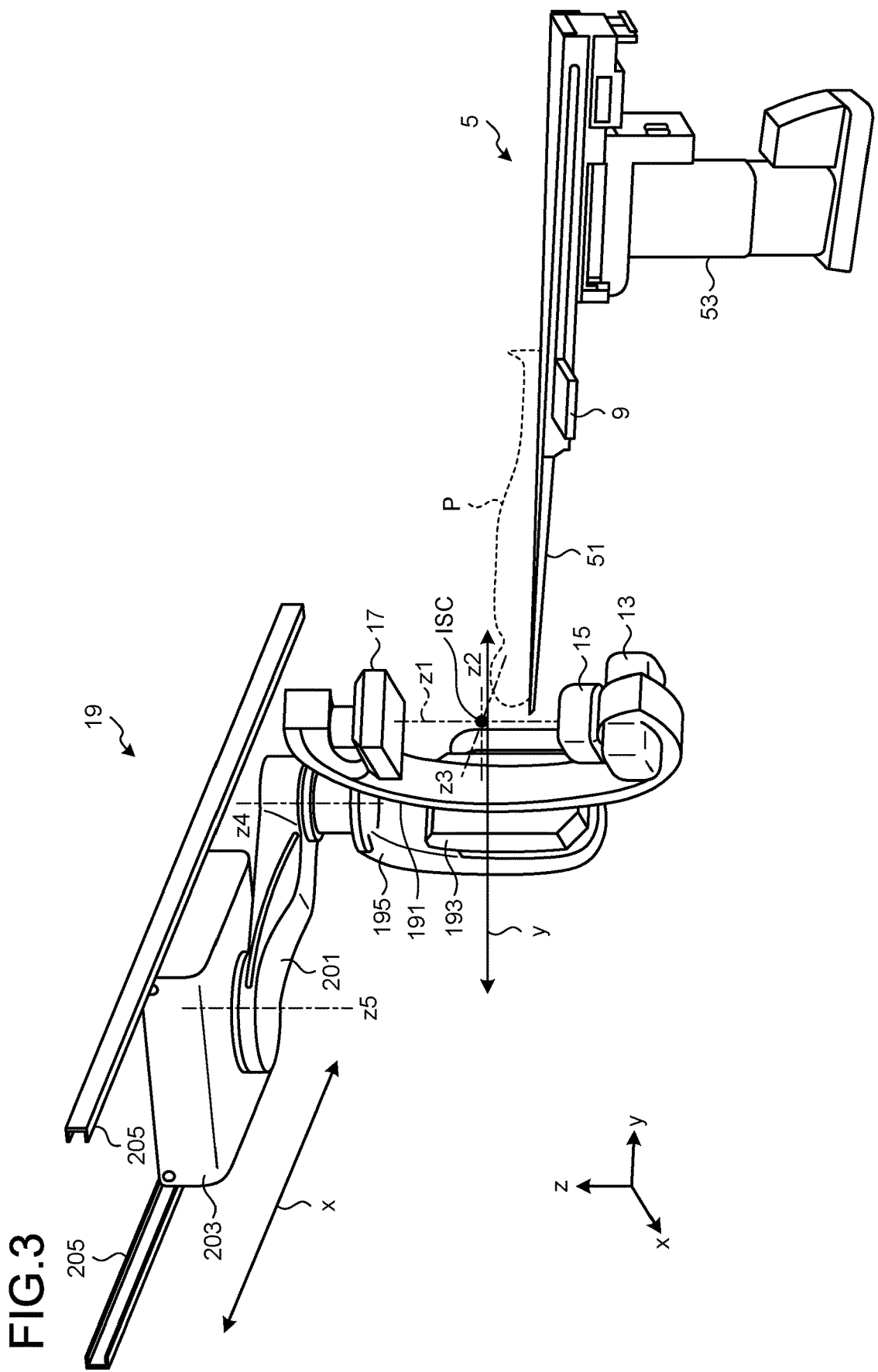
FIG. 3 is a drawing according to the embodiment illustrating examples of a ceiling-mounted holding device and the table.

Regarding an example in which the holding device 19 is of a ceiling-mounted type, the differences from FIG. 2 will briefly be explained with reference to FIG. 3. FIG. 3 is a drawing illustrating an example of the ceiling-mounted holding device 19 together with the table 5. A display device 251 and the like are omitted as appropriate from FIG. 3. As illustrated in FIG. 3, the floor turning arm 197 illustrated in FIG. 2 is supported, as a ceiling turning arm 201, by a base 203 so as to be rotatable on a rotation axis $z5$. As a result of an operation of the imaging system moving and driving unit 71, the ceiling turning arm 201 rotates on the rotation axis $z5$ (hereinafter, "rotation on the ceiling"). The base 203 is supported by a rail (hereinafter, "ceiling rail") 205 installed on the ceiling of the examination room, so as to be slidable along the direction (hereinafter, "rail direction"; the x direction in FIG. 3) parallel to the ceiling rail 205 and along the direction (hereinafter, "orthogonal-to-rail direction"; the y direction in FIG. 3) orthogonal to the rail direction. As a result of an operation of the imaging system moving and driving unit 71, the base 203 moves parallel to the rail direction or to the orthogonal-to-rail direction (hereinafter, "sliding on the ceiling").

With the arrangements described above, the holding device 19 is capable of moving the X-ray tube 13 and the X-ray detector 17 to arbitrary positions desired by the operator, with respect to the patient P. The holding device 19 does not necessarily need to have the rotation axes $z1$ to $z5$ illustrated in FIG. 2 and may have an arbitrary configuration. As a result of operations of the imaging system moving and driving unit 71 based on instructions from the operator via the maneuvering unit 9, the holding device 19 is configured to move the X-ray tube 13 and the X-ray detector 17.

The pedestal 53 is configured to support the tabletop 51 so as to be able to make parallel movement along the z-axis. As a result of an operation of the tabletop moving and driving unit 73, the pedestal 53 is configured to cause the tabletop 51 to make the parallel movement (hereinafter, "tabletop up-and-down movement") along the z-axis as indicated by the arrow g. The pedestal 53 is configured to support the tabletop 51 so as to be able to make parallel movement along the long-axis direction of the tabletop 51. As a result of an operation of the tabletop moving and driving unit 73, the pedestal 53 is configured to cause the tabletop 51 to make the parallel movement (hereinafter "tabletop sliding") along the long-axis direction of the tabletop 51 as indicated by the arrow h.

The pedestal 53 is configured to tiltably support the tabletop 51 on a rotation axis $z6$ being the long-axis direction of the tabletop 51. As a result of an operation of the tabletop moving and driving unit 73, the pedestal 53 is configured to tilt the tabletop 51 around the rotation axis $z6$ as indicate by the arrow j. The pedestal 53 is configured to tiltably support the tabletop 51 on a rotation axis $z7$ being the short-axis direction of the tabletop 51. As a result of an operation of the tabletop moving and driving unit 73, the pedestal 53 is configured to tilt the tabletop 51 around the rotation axis $z7$ as indicated by the arrow k. Hereinafter, operations related to tilting the tabletop 51 will be referred to as "tabletop tilting".

Figure 4:
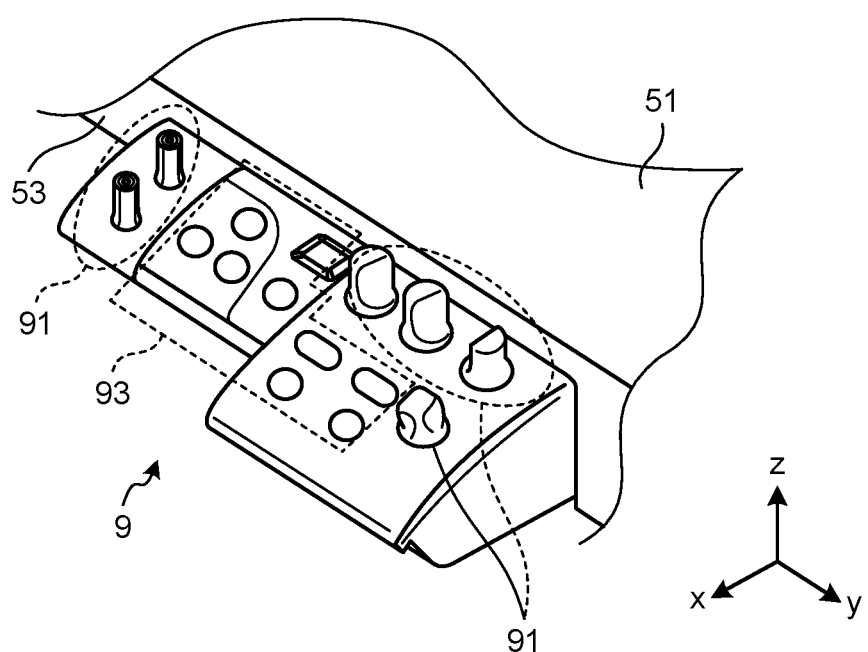
FIG. 4 is a drawing according to the embodiment illustrating an example of a maneuvering unit provided on a lateral face of the table.

FIG. 4 is a drawing illustrating an example of the maneuvering unit 9 provided on a lateral face of the table 5. The maneuvering unit 9 corresponds to a maneuver console used for maneuvering the X-ray diagnosis apparatus 1. The maneuvering unit 9 includes a handle unit 91 to be gripped by the operator and various types of switches 93. For example, the handle unit 91 is gripped by a thumb (pollex), an index finger (forefinger), and a middle finger of the operator. Alternatively, the handle unit 91 may be gripped by other fingers of the operator or may have fingers wrapped around. Further, the handle unit 91 may be held in a hand of the operator. As illustrated in FIG. 3, the handle unit 91 is a joystick. The maneuvering unit 9 is configured to receive a maneuver to bring into operation one or both of the imaging unit 3 and the table 5 according to an operation of the handle unit 91. In other words, the maneuvering unit 9 corresponds to a console configured to receive the maneuver to bring into operation the one or both of the imaging unit 3 and the table 5. The maneuvering unit 9 is configured to output an operation signal related to the operation on the handle unit 91 to the processing circuitry 21.

The handle unit 91 includes a plurality of contact detecting parts configured to detect contact of the operator with the handle unit 91. In other words, the plurality of contact detecting parts are incorporated in the handle unit 91. As the contact detecting parts, it is possible to use any of various types of contact sensors. To prevent erroneous detections caused by surgical covering cloth (a drape), it is desirable, for example, to use one or both of the following as the contact sensors: a pressure sensor configured to detect pressure caused by the contact; and a temperature sensor configured to detect temperature caused by the contact. The reasons is that the contact made by the drape has lower pressure than the contact made by the grip of the operator, the pressure sensor is able to distinguish between these two types of contact. Further, because the fingers of the operator have a higher temperature than that of the drape, the temperature sensor is also able to distinguish between the two types of contact. For example, the plurality of contact detecting parts are provided in at least two positions selected from among: a plurality of sections on one or more lateral faces of the handle unit 91 and a tip end part of the handle unit 91. For example, the plurality of contact detecting parts include a first contact detecting part and a second contact detecting part. The second contact detecting part is arranged in such a position where the contact detection is impossible when the operator comes into contact with the handle unit 91 only from one direction to be in contact with the first contact detecting part. The contact detecting parts are configured to output a detection signal related to the contact detection, to the processing circuitry 21. The detection signal corresponds to a detection result indicating whether contact has been made or not.

In the following sections, examples of the shape of the handle unit 91 and arrangement patterns of the plurality of contact detecting parts will be explained, with reference to FIGS. 5 to 11. The shapes of the handle unit 91 and the arrangement patterns of the plurality of contact detecting parts illustrated in FIGS. 5 to 11 are merely examples. It is possible to arbitrarily set any arrangement pattern, as long as one or more of the contact detecting parts are arranged in such positions where the contact detection is impossible when the operator comes into contact with the handle unit 91 from one direction.

Figure 5:
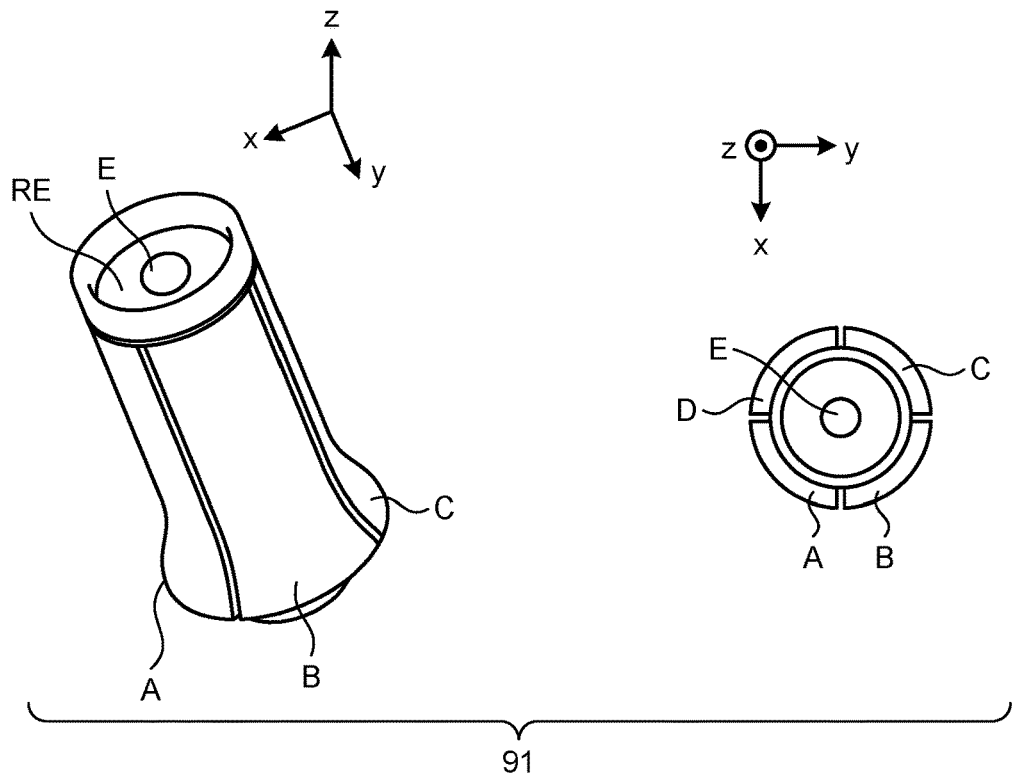
FIG. 5 is a drawing according to the embodiment illustrating an example of a handle unit, together with an arrangement pattern of a plurality of contact detecting parts.

FIG. 5 is a drawing illustrating an example of the handle unit 91, together with an arrangement pattern of a plurality of contact detecting parts A, B, C, D, and E. The plurality of contact detecting parts A, B, C, and D are arranged in four sections on the lateral face of the handle unit 91. Further, as illustrated in FIG. 5, the tip end of the handle unit 91 has a recessed part RE to facilitate placement of the fingers of the operator. The contact detecting part E is provided in a tip end part of the handle unit 91 in the recessed part RE. In another example, the recessed part RE may be omitted from the handle unit 91.

Figure 6:
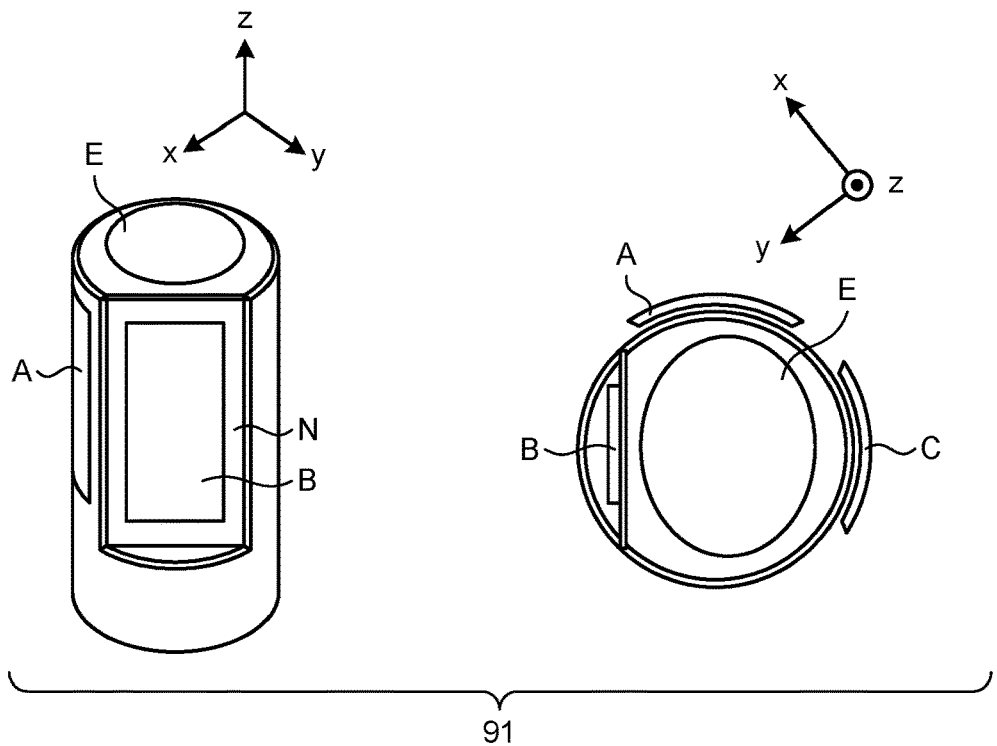
FIG. 6 is a drawing according to the embodiment illustrating another example of the handle unit, together with an arrangement pattern of a plurality of contact detecting parts.

FIG. 6 is a drawing illustrating another example of the handle unit 91, together with an arrangement pattern of the plurality of contact detecting parts A, B, C, D, and E. The handle unit 91 illustrated in FIG. 5 has a flat surface N formed by a cutout part, on the lateral face of the handle unit 91 having a circular cylindrical shape. In other words, a part of the lateral face of the handle unit 91 has the flat surface. In the handle unit 91 illustrated in FIG. 6, the contact detecting parts A and C are provided on the lateral face of the handle unit 91, while the contact detecting part E is provided in a tip end part of the handle unit 91. In addition, the contact detecting part B is provided on the flat surface N formed by the cutout part. The number of contact detecting parts arranged on the lateral face illustrated in FIG. 6 does not necessarily have to be two and may be two or more. For example, a thumb of the operator may be pressed against the flat surface N formed by the cutout part. In that situation, the lateral face of the handle unit 91 illustrated in FIG. 6 is held by the index finger and/or the middle finger of the operator.

Figure 7:
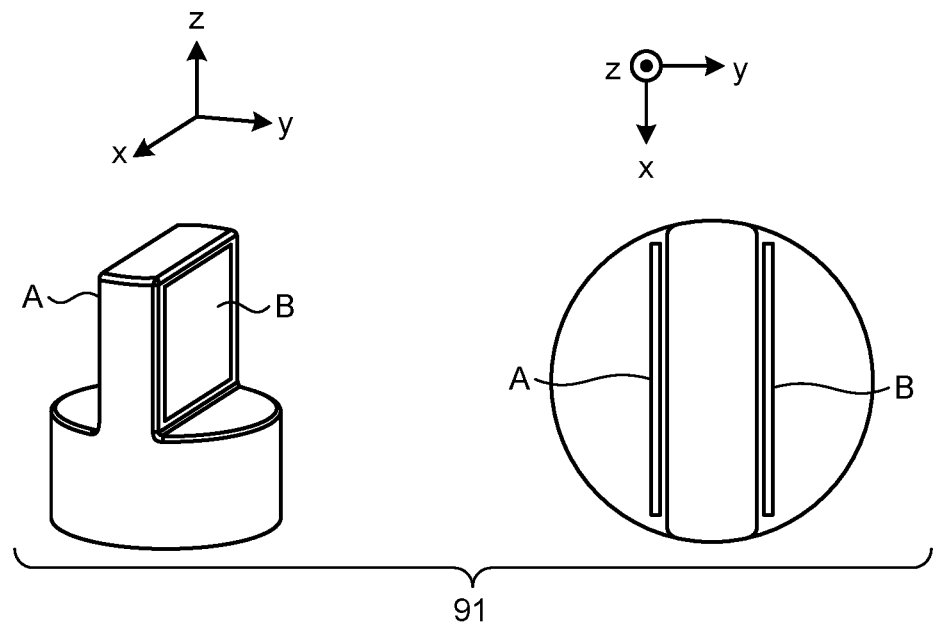
FIG. 7 is a drawing according to the embodiment illustrating yet another example of the handle unit, together with an arrangement pattern of a plurality of contact detecting parts.

FIG. 7 is a drawing illustrating yet another example of the handle unit 91, together with an arrangement pattern of a plurality of contact detecting parts A and B. The lateral face of the handle unit 91 illustrated in FIG. 7 has two flat surfaces extending parallel to each other. In this situation, for example, the handle unit 91 is expected to be maneuvered while being gripped by the two flat surfaces. For this reason, in the handle unit 91 illustrated in FIG. 7, the contact detecting parts A and B are arranged on the two flat surfaces opposing each other.

Figure 8:
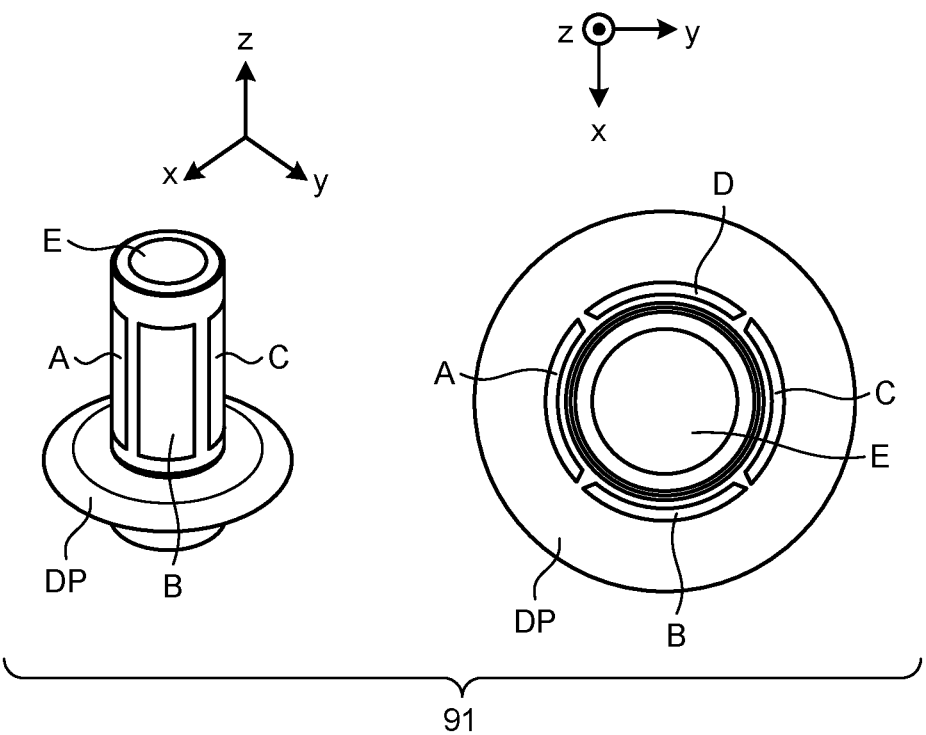
FIG. 8 is a drawing according to the embodiment illustrating an example of a handle unit having an umbrella-like drip-proof structure at the bottom thereof, together with an arrangement pattern of a plurality of contact detecting parts.

FIG. 8 is a drawing illustrating another example of the handle unit 91 having an umbrella-like drip-proof structure DP at the bottom thereof, together with an arrangement pattern of a plurality of contact detecting parts A, B, C, D, and E. The handle unit 91 illustrated in FIG. 8 is maneuvered while the drip-proof structure DP is avoided or while fingers of the operator are placed on the drip-proof structure DP. For this reason, in the handle unit 91 illustrated in FIG. 8, the plurality of contact detecting parts A, B, C, D, and E are arranged above the drip-proof structure DP. Because the arrangement pattern of the plurality of contact detecting parts A, B, C, D, and E illustrated in FIG. 8 is similar to that in FIG. 5, the explanation thereof will be omitted. The contact detecting part E in FIG. 8 is arranged on the flat surface in a tip end part of the handle unit 91.

Figure 9:
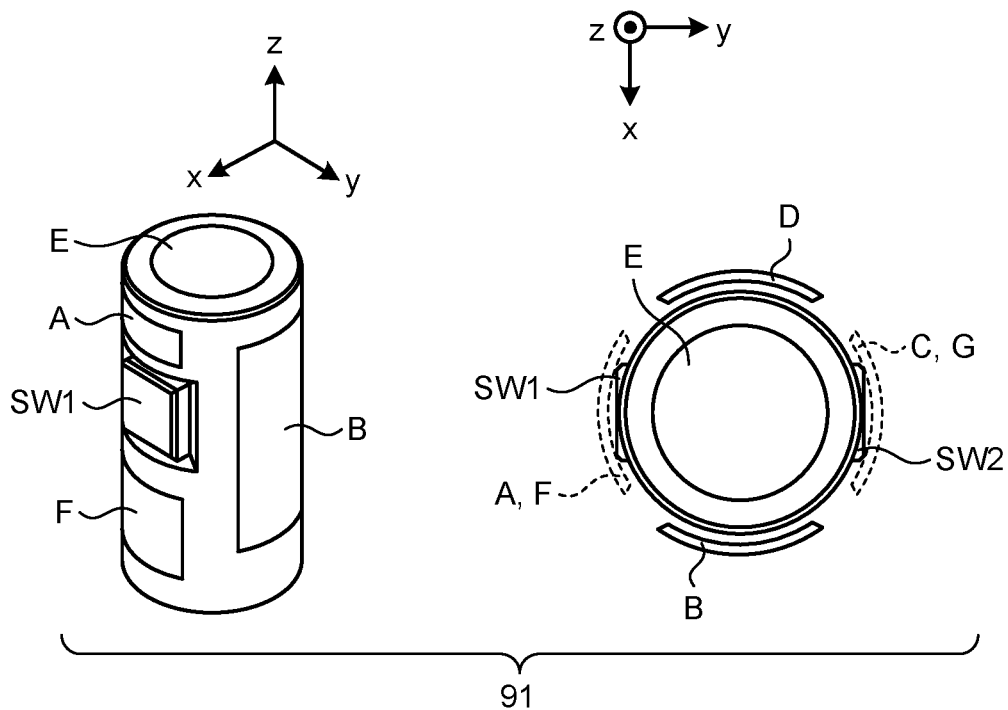
FIG. 9 is a drawing according to the embodiment illustrating a handle unit having two switches on the lateral face thereof, together with an arrangement pattern of a plurality of contact detecting parts.

FIG. 9 is a drawing illustrating an example of the handle unit 91 having two switches SW1 and SW2 on the lateral face thereof, together with an arrangement pattern of a plurality of contact detecting parts A, B, C, D, E, F, and G. The difference between FIG. 9 and FIG. 5 is that the contact detecting part A and the contact detecting part F are arranged above and below the switch SW1, respectively, while the contact detecting part C and the contact detecting part G are arranged above and below the switch SW2, respectively. Because the arrangement pattern of the contact detecting part B and the contact detecting part D in FIG. 9 is the same as that in FIG. 5, the explanation thereof will be omitted. The contact detecting part E in FIG. 9 is arranged on the flat surface in a tip end part of the handle unit 91.

Figure 10:
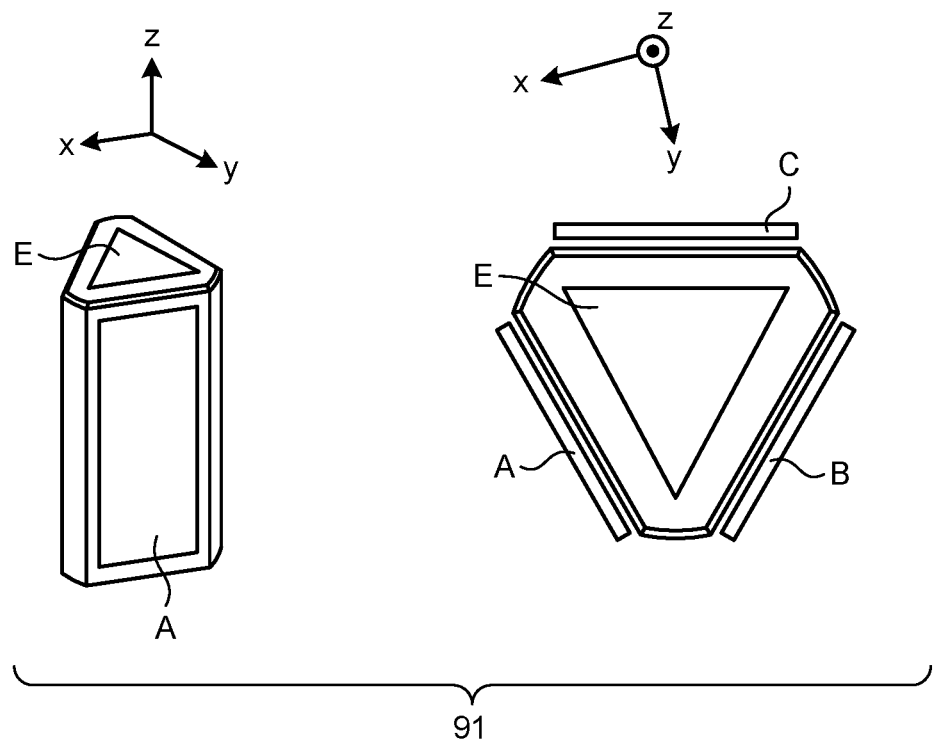
FIG. 10 is a drawing according to the embodiment illustrating a handle unit having a triangular prism shape, together with an arrangement pattern of a plurality of contact detecting parts.

FIG. 10 is a drawing illustrating an example of the handle unit 91 having a triangular prism shape, together with an arrangement pattern of a plurality of contact detecting parts A, B, C, and E. As illustrated in FIG. 10, each of the plurality of contact detecting parts A, B, and C is arranged on a different one of the three lateral faces of the handle unit 91. The contact detecting part E in FIG. 10 is arranged on a flat surface in a tip end part of the handle unit 91. Although FIG. 10 illustrates the example of the handle unit 91 having the triangular prism shape, the handle unit 91 may have any polygonal prism shape. In that situation, a plurality of contact detecting parts are arranged on the plurality of lateral faces of the polygonal prism and on a flat surface in the tip end part.

Figure 11:
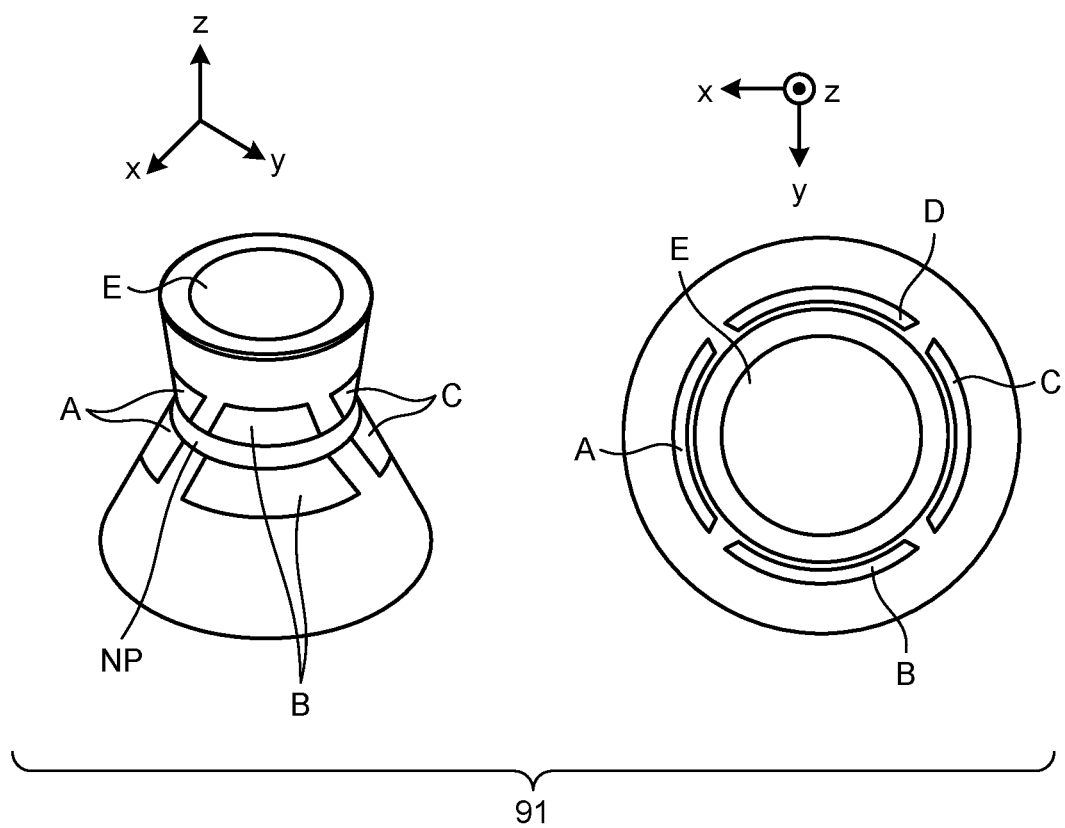
FIG. 11 is a drawing according to the embodiment illustrating a handle unit having a constricted part, together with an arrangement pattern of the plurality of contact detecting parts.

FIG. 11 is a drawing illustrating the handle unit 91 having a constricted part NP, together with an arrangement pattern of a plurality of contact detecting parts A, B, C, D, and E. As illustrated in FIG. 11, each of the plurality of contact detecting parts A, B, C, and D is arranged in the vicinity of the constricted part NP of the handle unit 91 so as to be positioned on either side of the constricted part NP. The contact detecting part E in FIG. 11 is arranged on a flat surface in a tip end part of the handle unit 91. For example, as illustrated in FIGS. 5, 6, and 8 to 11, the plurality of contact detecting parts include two contact detecting parts positioned apart from each other (hereinafter, distanced detecting parts) and two contact detecting parts positioned adjacent to each other.

The processing circuitry 21 is configured to control operations of the entirety of the X-ray diagnosis apparatus 1 in accordance with electrical signals of the input maneuvers output from either the maneuvering unit 9 or the input interface 27. For example, as hardware resources thereof, the processing circuitry 21 includes a processor such as a Central Processing Unit (CPU), a Micro Processing Unit (MPU), or a Graphics Processing Unit (GPU); and a memory such as a Read-Only Memory (ROM) or a Random Access Memory (RAM).

Various types of processing functions executed by the processing circuitry 21 are stored in the storage circuitry 23 in the form of computer-executable programs. The processing circuitry 21 is a processor configured to realize the functions corresponding to the programs by reading and executing the programs from the storage circuitry 23. In other words, the circuits that have read the programs have the functions corresponding to the read programs.

By employing the processor configured to execute the programs loaded into the memory, the processing circuitry 21 is configured to execute the controlling function 211, a judging function 212, and an image generating function 213. The processing circuitry 21 that executes the controlling function 211, the judging function 212, and the image generating function 213 corresponds to a controlling unit, a judging unit, and an image generating unit. Further, the controlling function 211, the judging function 212, and the image generating function 213 do not necessarily have to be realized with a single processing circuit. It is also acceptable to structure a processing circuitry by combining together a plurality of independent processors, so that the controlling function 211, the judging function 212, and the image generating function 213 are realized as a result of the processors executing the programs.

Further, the processing circuitry 21 may be realized by using a processor such as an Application Specific Integrated Circuit (ASIC), a Field Programmable Gate Array (FPGA), any other Complex Programmable Logic Device (CPLD), or a Simple Programmable Logic Device (SPLD).

By employing the controlling function 211, the processing circuitry 21 is configured to control the driving unit 7, the X-ray high-voltage device 11, the X-ray limiter 15, the storage circuitry 23, the display unit 25, the image generating function 213, and the like, on the basis of input maneuvers received from the operator via either the maneuvering unit 9 or the input interface 27. More specifically, the controlling function 211 is configured to read a control program stored in the storage circuitry 23, to load the read program into a memory within the processing circuitry 21, and to control functional units of the X-ray diagnosis apparatus 1 according to the loaded control program. A process (hereinafter, "drive controlling process") of controlling the driving unit 7 on the basis of input signals received via the maneuvering unit 9 will be explained later.

On the basis of a plurality of detection results obtained by the plurality of contact detecting parts, the processing circuitry 21 is configured to judge, by employing the judging function 212, whether or not one or both of the imaging unit 3 and the table 5 are to be brought into operation. More specifically, upon the input of an operation signal while being in a state of receiving a detection signal, the processing circuitry 21 determines that it is possible to bring one or both of the imaging unit 3 and the table 5 into operation. Processes performed by the judging function 212 in the procedure of the drive controlling process will be explained later.

By employing the image generating function 213, the processing circuitry 21 is configured to generate image data on the basis of an output of the X-ray detector 17. More specifically, the processing circuitry 21 is configured to generate projection data on the basis of the output of the X-ray detector 17. Subsequently, upon receipt of an input signal either from the maneuvering unit 9 or the input interface 27, the processing circuitry 21 is configured to generate the image data by performing an image processing process such as a filtering process on the projection data. The image data corresponds to data of medical images including one or more fluoroscopic images and/or captured images related to the patient P. The processing circuitry 21 is configured to perform a combining process, a subtraction process, and/or the like by using the image data. The processing circuitry 21 is configured to output the generated image data to the storage circuitry 23 and/or to the display unit 25.

The storage circuitry (memory) 23 is a storage device such as a Hard Disk Drive (HDD), a Solid State Drive (SDD), or an integrated circuit storage device storing therein various types of information. For example, the storage circuitry 23 is configured to store therein the projection data, the image data, and the programs corresponding to the various types of functions and being read and executed by the processing circuitry 21. Instead of being an HDD or an SDD, the storage circuitry 23 may be a driving device configured to read and write various types of information from and to a portable storage medium such as a Compact Disc (CD), a Digital Versatile Disc (DVD), or a flash memory, or a semiconductor memory element such as a Random Access Memory (RAM). Further, a saving area of the storage circuitry 23 may be in an external storage device connected via a network.

The display unit 25 is structured by using a display device 251 configured to display a medical image g1 and the like; an internal circuit configured to supply the display device 251 with a display-purpose signal; and a peripheral circuit including a connector and a cable connecting the display device 251 to the internal circuit. The internal circuit is configured to generate display data by superimposing additional information such as patient information and a projection data generating condition, on the image data. Subsequently, the internal circuit applies a D/A conversion and a TV format conversion to the obtained display data. The internal circuit is configured to cause the display device 251 to display the display data resulting from the conversions as the medical image g1. In addition, the display unit 25 is configured to display a Graphical User Interface (GUI) or the like used for receiving various types of maneuvers from the operator, in a display region g2.

As the display device 251, it is possible to use, for example, a Liquid Crystal Display (LCD) device, a Cathode Ray Tube (CRT) display device, an Organic Electroluminescence Display (GELD) device, a plasma display device, or any other arbitrary display device, as appropriate. Further, the display device 251 may be of a desktop type or may be configured by using a tablet terminal or the like capable of wirelessly communicating with the processing circuitry 21.

The input interface 27 is configured to receive various types of input maneuvers from the operator, to convert the received input maneuvers into electrical signals, and to output the electrical signals to the processing circuitry 21. For example, the input interface 27 is configured to receive, from the operator, a maneuver to bring one or both of the imaging unit 3 and the table 5 into operation, an X-ray condition related to the generation of the X-rays, a condition related to image processing processes performed by the image generating function 213, and the like. As the input interface 27, for example, it is possible to use a mouse, a keyboard, a trackball, a switch, a button, a joystick, a foot switch, a touchpad, a touch panel display device, and/or the like, as appropriate. For example, the input interface 27 is incorporated in a console device installed in a control room different from the examination room. In this situation, the joystick realized as the input interface 27 may have any of the structures illustrated in FIGS. 5 to 11. Alternatively, the input interface 27 may be provided for the holding device 19.

In the present embodiment, the input interface 27 does not necessarily have to include one or more physical operational component parts such as a mouse, a keyboard, a trackball, a switch, a button, a joystick, a touchpad, a touch panel display device, and/or the like. Examples of the input interface 27 include, for instance, an electrical signal processing circuit configured to receive an electrical signal corresponding to an input maneuvers from an external input device provided separately from the apparatus and to output the electrical signal to the processing circuitry 21. Alternatively, the input interface 27 may be configured by using a tablet terminal or the like capable of wirelessly communicating with the processing circuitry 21.

An overall configuration of the X-ray diagnosis apparatus 1 according to the embodiment has thus been explained. The X-ray diagnosis apparatus 1 according to the embodiment structured as described above is configured to perform the drive controlling process. The drive controlling process is a process of judging, by employing the judging function 212, whether or not one or both of the imaging unit 3 and the table 5 are to be brought into operation on the basis of the plurality of detection results (i.e., whether contact is made or not) obtained by the plurality of contact detecting parts and further implementing, by employing the controlling function 211, at least one of the following operations: moving the supporting arm 191, changing the exterior shape of the supporting arm 191, and moving the tabletop 51, in response to a maneuver performed on the handle unit 91 accompanied by the contact detection.

For example, the moving of the supporting arm 191 corresponds to at least one of: rotating the supporting arm 191 (the main rotation, the columnar rotation, the rotation on the floor, or the rotation on the ceiling) with respect to a rotation axis; sliding of the supporting arm 191 (the C-arm sliding); and translation of the supporting position in which the supporting arm 191 is supported (the sliding on the ceiling). Further, the changing of the exterior shape of the supporting arm 191 corresponds to at least one of: changing the distance (the SID) between the X-ray tube 13 and the X-ray detector 17 (an SID change); and the X-ray detector 17 rotating with respect to the X-ray tube 13 (the detector rotation). Further, the moving of the tabletop 51 corresponds to at least one of: translation along the vertical direction (the tabletop up-and-down movement); sliding with respect to the table 5 (the tabletop sliding); and the tabletop 51 tilting with respect to a horizontal plane (the tabletop tilting).

More specifically, upon the input of an operation signal while being in the state of receiving a detection signal, the processing circuitry 21 is configured, by employing the judging function 212, to determine that it is possible to bring one or both of the imaging unit 3 and the table 5 into operation. Subsequently, upon the input of an operation signal while being in a state of receiving a detection signal, the processing circuitry 21 is configured, by employing the controlling function 211, to output a drive signal to drive one of the imaging unit 3 and the table 5 to the driving unit 7, in accordance with the operation signal. More specifically, when the handle unit 91 has an operation while any pair of distanced detecting parts among the plurality of contact detecting parts is detecting contact made by the operator, the processing circuitry 21 is configured, by employing the controlling function 211, to output the drive signal to bring into operation one or both of the imaging unit 3 and the table 5 to the driving unit 7 that drives the one or both of the imaging unit 3 and the table 5 corresponding to the operation of the handle unit 91.

Figure 12:
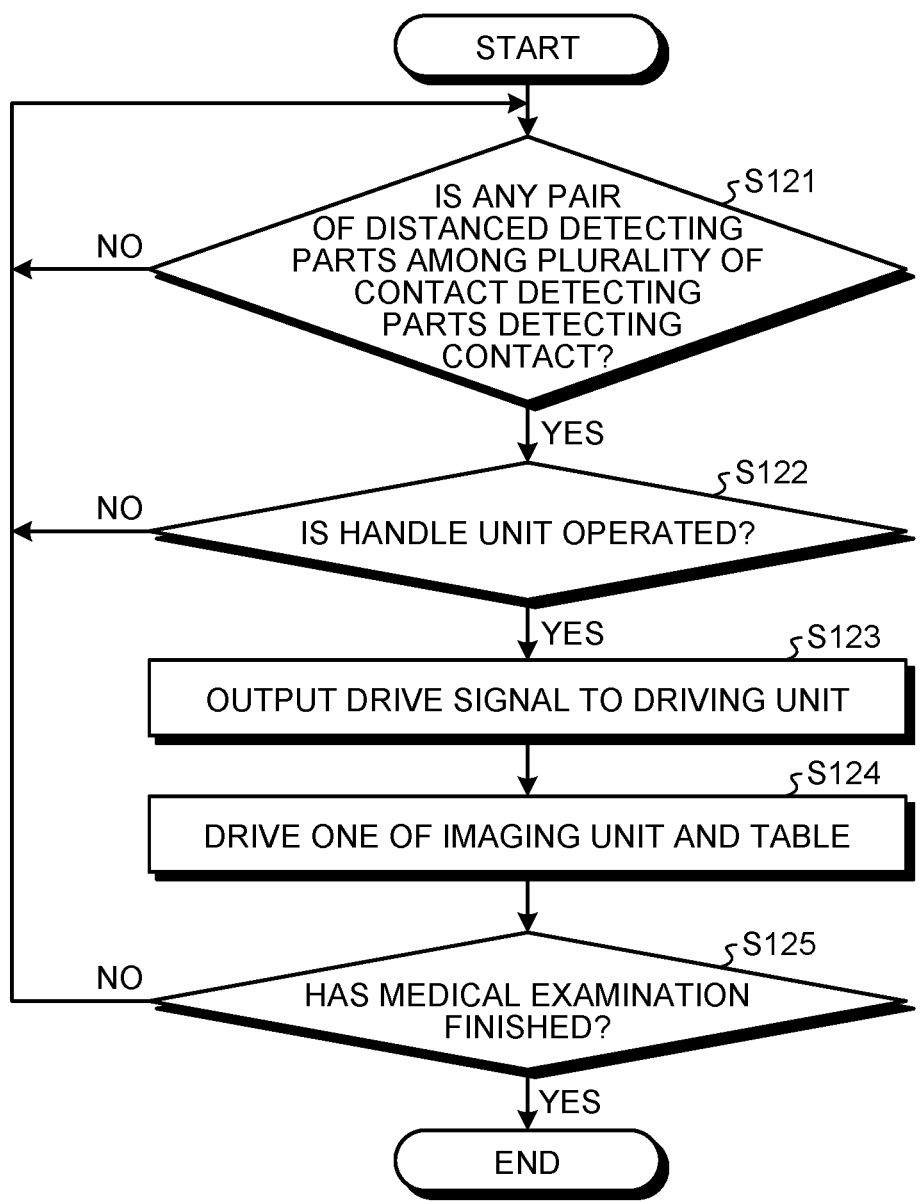
FIG. 12 is a flowchart according to the embodiment illustrating an example of a procedure in a drive controlling process.

In the following sections, a procedure in the drive controlling process will be explained, with reference to FIG. 12. FIG. 12 is a flowchart illustrating an example of the procedure in the drive controlling process. To explain the example more specifically, let us assume that the shape of the handle unit 91 and the arrangement pattern of the plurality of contact detecting parts are those illustrated in FIG. 5.

The drive controlling process

The operator comes into contact with the handle unit 91. In this situation, before coming into contact with the handle unit 91, the operator may select, by using one of the switches 93 in the maneuvering unit 9, a moved target or a moving operation subject to the maneuver on the handle unit 91. The moved target may be, for example, the X-ray detector 17, the SID, the C-arm 191, the arm holder 193, the stand 195, the floor turning arm 197, the a-shaped arm, the ceiling turning arm 201, the base 203, the tabletop 51, or the like. The moving operation indicates specifics of a conjunctive movement made by a combination of the abovementioned moved targets (e.g., a widthwise movement of the C-arm 191 (a parallel movement of the X-ray detector 17 along the x direction); or a lengthwise movement of the C-arm 191 (a parallel movement of the X-ray detector 17 along the y direction)).

Figure 13:
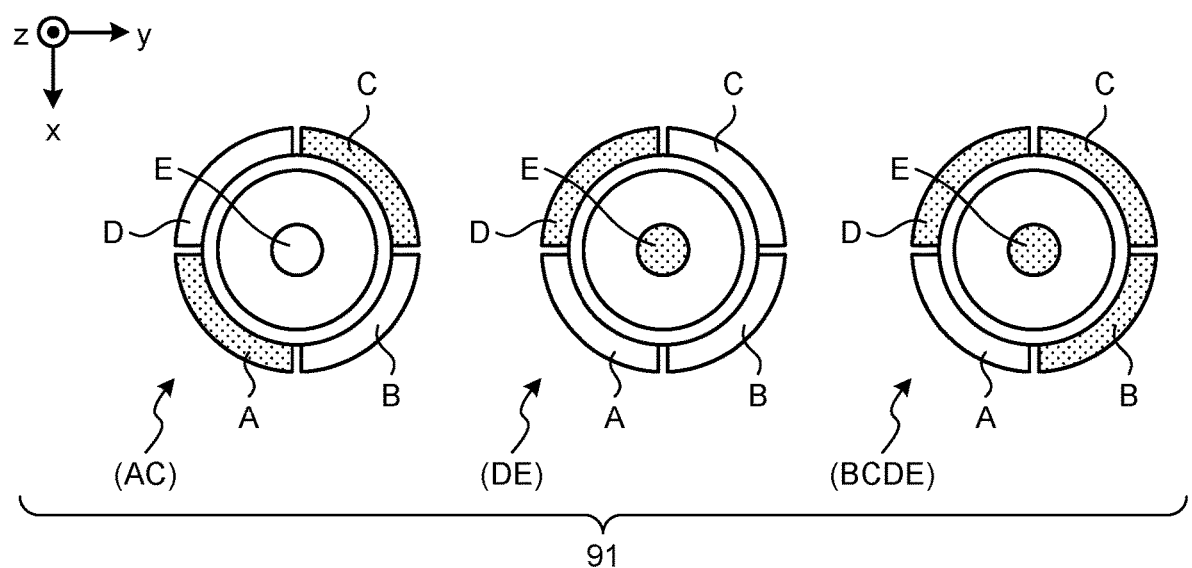
FIG. 13 is a drawing according to the embodiment illustrating examples of contact detection by distanced detecting parts.

Step S121:

At least one of the plurality of contact detecting parts A, B, C, D, and E detects the contact made by the operator. The contact detecting part outputs a detection signal derived from the contact to the processing circuitry 21. By employing the controlling function 211, the processing circuitry 21 judges whether or not any pair of distanced detecting parts among the plurality of contact detecting parts has detected contact. FIG. 13 is a drawing illustrating examples of contact detection by distanced detecting parts. In FIG. 13, "(AC)" indicates that the contact detecting part A and the contact detecting part C have detected contact and that distanced detecting parts represented by the contact detecting part A and the contact detecting part C have thus detected the contact. Further, in FIG. 13, "(DE)" indicates that the contact detecting part D and the contact detecting part E have detected contact and that distanced detecting parts represented by the contact detecting part D and the contact detecting part E have thus detected the contact. Also, in FIG. 13, "(BCDE)" indicates that the contact detecting part B, the contact detecting part C, the contact detecting part D, and the contact detecting part E have detected contact and that distanced detecting parts represented by the contact detecting part B and the contact detecting part D; distanced detecting parts represented by the contact detecting part B and the contact detecting part E; distanced detecting parts represented by the contact detecting part C and the contact detecting part E; and distanced detecting parts represented by the contact detecting part D and the contact detecting part E each have thus detected the contact.

When none of the distanced detecting parts has detected contact (step S121: No), the processing circuitry 21 is in a standby state waiting to receive a detection signal from any pair of distanced detecting parts. In that situation, even when the handle unit 91 has an operation, the processing circuitry 21 outputs no drive signal to the driving unit 7. In other words, by employing the controlling function 211, the processing circuitry 21 outputs no drive signal to the driving unit 7 in the situation where the handle unit 91 has an operation while none of the distanced detecting parts is detecting contact made by the operator. When any pair of distanced detecting parts has detected contact (step S121: Yes), the process at step S122 will be performed.

After the process at step S121 is performed, the display unit 25 may display whether or not the handle unit 91 is able to operate the imaging unit 3 and the table 5, on the basis of the judgment result from the judging function 212. For example, when any pair of distanced detecting parts has detected contact, the display device 251 may display, in the display region g2, information indicating that the handle unit 91 is able to operate the imaging unit 3 and the table 5. On the contrary, when none of the distanced detecting parts has detected contact, the display device 251 displays, in the display region g2, information indicating that the handle unit 91 is not able to operate the imaging unit 3 and the table 5.

Step S122:

When the handle unit 91 is maneuvered while one or more pairs of distanced detecting parts are detecting contact (step S122: Yes), the process at step S123 is performed. When the handle unit 91 is not maneuvered while one or more pairs of distanced detecting parts are detecting contact (step S122: No), the process at step S121 will be performed.

Step S123:

By employing the controlling function 211, the processing circuitry 21 outputs, on the basis of an operation signal, a drive signal to bring the driving unit 7 into operation to the driving unit 7. For example, when the handle unit 91 has input an operation related to the detector rotation or the SID change, the processing circuitry 21 outputs the drive signal to the imaging system moving and driving unit 71 provided for the C-arm 191. When the handle unit 91 has input an operation related to the C-arm sliding, the processing circuitry 21 outputs the drive signal to the imaging system moving and driving unit 71 provided for the arm holder 193. When the handle unit 91 has input an operation related to the main rotation, the processing circuitry 21 outputs the drive signal to the imaging system moving and driving unit 71 provided for the stand 195. When the handle unit 91 has input an operation related to the columnar rotation or the rotation on the floor, the processing circuitry 21 outputs the drive signal to the imaging system moving and driving unit 71 provided for the floor turning arm 197.

Further, when the handle unit 91 has input an operation related to the rotation on the ceiling or the sliding on the ceiling, the processing circuitry 21 outputs the drive signal to the imaging system moving and driving unit 71 provided for the base 203. When the handle unit 91 has input an operation related to the tabletop up-and-down movement, the tabletop sliding, or tabletop tilting, the processing circuitry 21 outputs the drive signal to the tabletop moving and driving unit 73 provided for the pedestal 53.

Further, when the handle unit 91 has input an operation related to specifics of a conjunctive movement, the processing circuitry 21 outputs the drive signal to the imaging system moving and driving unit 71 related to the specifics of the conjunctive movement. For example, when the handle unit 91 has input an operation related to a widthwise movement of the C-arm 191 or a lengthwise movement of the C-arm 191, the processing circuitry 21 outputs the drive signal to the imaging system moving and driving unit 71 provided for the floor turning arm 197 and to the imaging system moving and driving unit 71 provided for the C-arm 191.

Step S124:

According to the drive signal, the driving unit 7 drives one of the imaging unit 3 and the table 5. For example, when the drive signal related to the detector rotation is output to the imaging system moving and driving unit 71 provided for the C-arm 191, the C-arm 191 executes the detector rotation. When the drive signal related to the SID change is output to the imaging system moving and driving unit 71 provided for the C-arm 191, the C-arm 191 executes the SID change. In another example, when the drive signal related to the C-arm sliding is output to the imaging system moving and driving unit 71 provided for the arm holder 193, the arm holder 193 executes the C-arm sliding. When the drive signal related to the main rotation is output to the imaging system moving and driving unit 71 provided for the stand 195, the stand 195 executes the main rotation. When the drive signal related to the columnar rotation is output to the imaging system moving and driving unit 71 provided for the floor turning arm 197, the floor turning arm 197 executes the columnar rotation. When the drive signal related to the rotation on the floor is output to the imaging system moving and driving unit 71 provided for the floor turning arm 197, the floor turning arm 197 executes the rotation on the floor.

In yet another example, when the drive signal related to the rotation on the ceiling is output to the imaging system moving and driving unit 71 provided for the base 203, the base 203 executes the rotation on the ceiling. When the drive signal related to the sliding on the ceiling is output to the imaging system moving and driving unit 71 provided for the base 203, the base 203 executes the sliding on the ceiling. When the drive signal related to the specifics of the conjunctive movement is output to the imaging system moving and driving unit 71, the holding device 19 executes the specifics of the conjunctive movement. For example, when the drive signal related to a widthwise movement of the C-arm 191 or a lengthwise movement of the C-arm 191 is output to the imaging system moving and driving unit 71, the floor turning arm 197 executes the rotation on the floor and the columnar rotation, and also, the C-arm 191 executes the detector rotation.

When the drive signal related to the tabletop up-and-down movement is output to the tabletop moving and driving unit 73, the pedestal 53 executes the tabletop up-and-down movement. When the drive signal related to the tabletop sliding is output to the tabletop moving and driving unit 73, the pedestal 53 executes the tabletop sliding. When the drive signal related to the tabletop tilting is output to the tabletop moving and driving unit 73, the pedestal 53 executes the tabletop tilting.

Step S125:

When the medical examination for the patient P has finished (step S125: Yes), the drive controlling process ends. On the contrary when the medical examination on the patient P has not finished (step S125: No), the processes at steps S121 through S125 will be repeatedly performed.

In the X-ray diagnosis apparatus 1 according to the embodiment described above, through the operation of the handle unit 91 including the plurality of contact detecting parts to detect the contact made by the operator and being gripped by the operator, the maneuver is received by which one or both of the following are brought into operation: the table 5 including the tabletop 51 on which the patient P is placed; and the imaging unit 3 including the X-ray tube 13 configured to radiate the X-rays onto the patient P and the X-ray detector 17 configured to detect the X-rays. It is judged whether or not one or both of the imaging unit 3 and the table 5 are to be brought into operation, on the basis of the plurality of detection results obtained by the plurality of contact detection parts. In accordance with the maneuver and the judgment result, the one or both of the imaging unit 3 and the table 5 is brought into operation. The plurality of contact detecting parts include the first contact detecting part and the second contact detecting part. The second contact detecting part is arranged in such a position where the contact detection is impossible when the operator comes into contact with the handle unit 91 only from one direction to be in contact with the first contact detecting part. For example, the plurality of contact detecting parts are arranged in at least two positions selected from among: the plurality of sections on one or more lateral faces of the handle unit 91 and the tip end part of the handle unit 91.

With these arrangements, by using the X-ray diagnosis apparatus 1 described above, when the handle unit 91 has an operation while any pair of contact detecting parts positioned apart from each other (the distanced detecting parts) among the plurality of contact detecting parts is detecting contact made by the operator, it is possible to output the drive signal bringing one or both of the imaging unit 3 and the table 5 into operation, to the driving unit 7 configured to drive the one or both of the imaging unit 3 and the table 5 corresponding to the operation of the handle unit 91. In addition, by using the X-ray diagnosis apparatus 1 described above, it is possible to refrain from outputting the drive signal to the driving unit 7 when the handle unit 91 has an operation while none of the distanced detecting parts is detecting contact made by the operator or when the distanced detecting parts no longer detect contact during an operation of the handle unit 91. With these arrangements, by using the X-ray diagnosis apparatus 1 described above, it is possible to prevent erroneous operations caused by coming into contact, from one direction, with the joystick corresponding to the handle unit 91. It is therefore possible to prevent erroneous operations of the X-ray diagnosis apparatus 1 (operations of the X-ray diagnosis apparatus 1 that are not intended by the practitioner) caused by an arm or a leg of the patient P or the abdomen of the practitioner coming into contact, while it is possible to maneuver the joystick, without the operator feeling trouble or cumbersomeness other than tilting the joystick. As a result, according to the present embodiment, it is possible to improve operability of the X-ray diagnosis apparatus 1, while ensuring secure feelings of the operator related to maneuvering the lever.

First Modification Example

In the present modification example, when the handle unit 91 has an operation while any pair of distanced detecting parts is detecting contact, and subsequently, the distanced detecting parts stop detecting the contact while the handle unit 91 is being operated (hereinafter, "non-detection during an operation"), one of the imaging unit 3 and the table 5 is brought into operation if the handle unit 91 is in operation. In a procedure of a drive controlling process in the present modification example, the process at step S122 is performed after the judgment result at step S125 is determined to be in the negative in FIG. 12. Even in the situation of the non-detection during an operation, the processing circuitry 21 outputs, by employing the controlling function 211, the drive signal to the driving unit 7 as long as the handle unit 91 is in operation. With this arrangement, by using the X-ray diagnosis apparatus 1 according to the first modification example, it is possible to drive the one of the imaging unit 3 and the table 5, even when the fingers of the operator come out of contact with the distanced detecting parts while the handle unit 91 is in operation, for example. With these arrangements, by using the X-ray diagnosis apparatus 1 according to the first modification example, it is possible to further improve operability of the X-ray diagnosis apparatus 1 while ensuring the secure feelings of the operator related to maneuvering the lever. Because the other details and the advantageous effects of the drive controlling process are the same as those of the above embodiment, the explanation thereof will be omitted.

Second Modification Example

In the present modification example, the maneuvering unit 9 is configured to judge whether or not any pair of distanced detecting parts has detected contact. The maneuvering unit 9 further includes a processor (a judging unit) configured to execute the judging function 212. When any pair of distanced detecting parts inputs a detection signal, the processor is configured, by employing the judging function 212, to determine that it is possible to bring one of the imaging unit 3 and the table 5 into operation. When the handle unit 91 is operated while it has been determined possible to bring into operation the one of the imaging unit 3 and the table 5, the maneuvering unit 9 is configured to output an operation signal related to the operation of the handle unit 91, to the processing circuitry 21. By employing the controlling function 211, the processing circuitry 21 is configured to output a drive signal based on the operation signal, to the driving unit 7. According to the present modification example, by replacing the console attached to the table 5 in an arbitrary X-ray diagnosis apparatus with the maneuvering unit 9 of the present modification example, it is possible to realize the technical features of the present modification example in the arbitrary X-ray diagnosis apparatus. Because the other details and the advantageous effects of the drive controlling process are the same as those of the above embodiment, the explanation thereof will be omitted.

An application example

Figure 14:
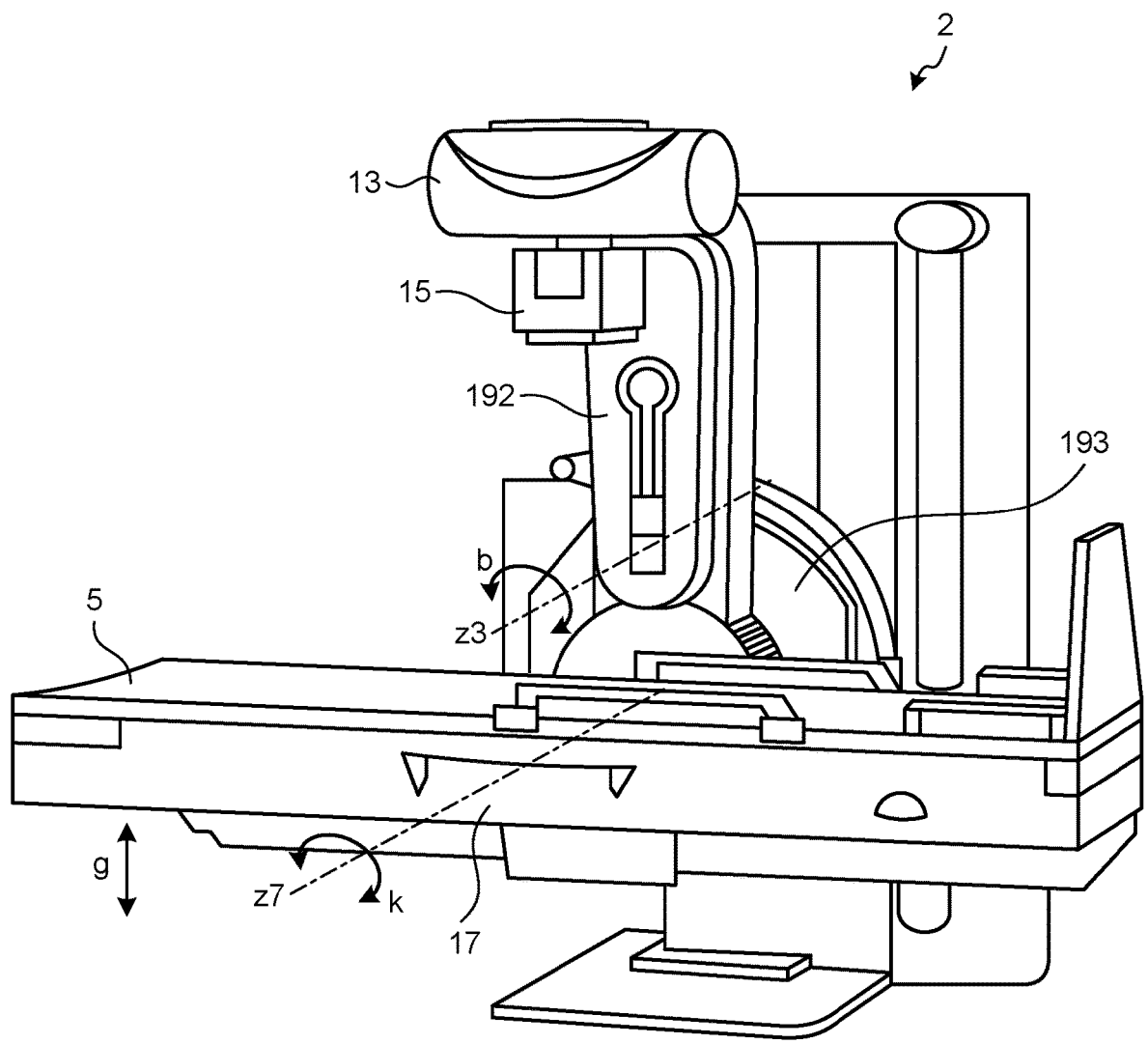
FIG. 14 is a drawing illustrating an example of external appearance of an X-ray TV apparatus according to an application example of the embodiment.

In the present application example, the drive controlling process is performed by an X-ray TV apparatus. In this situation, as contact sensors realizing the contact detecting parts of the X-ray TV apparatus, electrostatic sensors or infrared sensors may be used. FIG. 14 is a drawing illustrating an example of the external appearance of an X-ray TV apparatus 2. As illustrated in FIG. 14, the table 5 has the X-ray detector 17 mounted thereon. Further, the supporting arm 192 has the X-ray tube 13 mounted thereon. In addition, the supporting arm 192 is connected to the table 5. While any pair of distanced detecting parts is detecting contact, when the handle unit 91 inputs an operation related to rotation of the supporting arm 192, the processing circuitry 21 outputs a drive signal to the imaging system moving and driving unit 71 provided for the supporting arm 192. In another example, while any pair of distanced detecting parts is detecting contact, when the handle unit 91 inputs an operation related to moving the table 5 (e.g., to be positioned upright/flat or rotated), the processing circuitry 21 outputs a drive signal to the tabletop moving and driving unit 73 provided for the table 5. Because the advantageous effects of the present application example are the same as those of the above embodiment, the explanation thereof will be omitted. Further, because features of an X-ray TV apparatus having the C-arm 191 are the same as those described in the embodiment and the present application example, the explanation thereof will be omitted.

When technical concepts of the present embodiment are realized in an X-ray diagnosis apparatus maneuvering device (the maneuvering unit 9), the X-ray diagnosis apparatus maneuvering device is configured to receive, as being gripped by an operator, a maneuver to bring into operation one or both of: the table 5 including the tabletop 51 on which the patient P is placed; and the imaging unit 3 including the X-ray tube 13 configured to radiate the X-rays onto the patient P and the X-ray detector 17 configured to detect X-rays, so that contact made by the operator is detected in a plurality of sections provided in a plurality of locations on the handle unit 9 and positioned apart from each other. A plurality of detection results related to the contact are output to the X-ray diagnosis apparatus 1 including the imaging unit 3 and the table 5. Because the advantageous effects of the X-ray diagnosis apparatus maneuvering device are the same as those of the embodiment, the explanation thereof will be omitted.

According to at least one aspect of the embodiments, the modification examples, the application example, and the like described above, it is possible to improve the operability while preventing operations that are not intended by the operator, regarding the X-ray diagnosis apparatus 1.

While certain embodiments have been described, these embodiments have been presented by way of example only, and are not intended to limit the scope of the inventions. The embodiments described herein may be embodied in a variety of other forms; furthermore, various omissions, substitutions, changes, and combinations in the form of the embodiments described herein may be made without departing from the spirit of the inventions. The accompanying claims and their equivalents are intended to cover such forms or modifications as would fall within the scope and spirit of the inventions.

In relation to the above embodiments, the following notes are presented as certain aspects and optional characteristics of the present disclosure:

Note 1:

An X-ray diagnosis apparatus including:

a table including a tabletop on which a patient is placed;

an imaging unit including an X-ray tube configured to radiate X-rays onto the patient and an X-ray detector configured to detect X-rays;

a maneuvering unit including a handle unit that is provided with a plurality of contact detecting parts to detect contact made by an operator and that is gripped by the operator and being configured to receive a maneuver to bring into operation one or both of the imaging unit and the table according to an operation of the handle unit; and a judging unit configured to judge whether or not one or both of the imaging unit and the table is to be brought into operation on the basis of a plurality of detection results obtained by the plurality of contact detecting parts; and a controlling unit configured to bring the one or both of the imaging unit and the table into operation in accordance with a result of the judgment by the judging unit and the maneuver performed on the maneuvering unit.

Note 2:

The imaging unit may further include a supporting arm configured to support the X-ray tube, with or without supporting the X-ray detector.

In response to the maneuver performed on the handle unit accompanied by the contact detection, the controlling unit may implement at least one of the following operations: moving the supporting arm; changing the exterior shape of the supporting arm; and moving the tabletop.

Note 3:

The moving of the supporting arm may correspond to at least one of: rotating of the supporting arm with respect to a rotation axis; sliding of the supporting arm; and translation of a supporting position in which the supporting arm is supported.

The changing of the exterior shape may correspond to at least one of: changing the distance between the X-ray tube and the X-ray detector; and rotating of the X-ray detector with respect to the X-ray tube.

The moving of the tabletop may correspond to at least one of: translation along the vertical direction; sliding with respect to the table; and tilting of the tabletop with respect to a horizontal plane.

Note 4:

When the handle unit has an operation while two contact detecting parts positioned apart from each other among the plurality of contact detecting parts are detecting the contact made by the operator, the controlling unit may output a drive signal to bring the one or both of the imaging unit and the table into operation, to a driving unit configured to drive the one or both of the imaging unit and the table corresponding to the operation of the handle unit.

Note 5:

When the handle unit has an operation while the two contact detecting parts are detecting no contact made by the operator, the controlling unit may be configured so as not to output the drive signal to the driving unit.

Note 6:

The plurality of contact detecting parts include a first contact detecting part and a second contact detecting part.

The second contact detecting part may be arranged in such a position where the contact detection is impossible when the operator comes into contact with the handle unit only from one direction to be in contact with the first contact detecting part.

Note 7:

The plurality of contact detecting parts may be arranged in at least two positions selected from among: a plurality of sections on one or more lateral faces of the handle unit and a tip end part of the handle unit.

Note 8:

The contact detecting parts may be configured to output a detection signal related to the contact detection to the judging unit.

The maneuvering unit may be configured to output an operation signal related to the operation of the handle unit to the controlling unit.

Upon the input of an operation signal while being in a state of receiving the detection signal, the judging unit may determine that it is possible to bring the one or both of the imaging unit and the table into operation.

Note 9:
A driving unit configured to drive the imaging unit and the table may further be provided.

Upon the input of the operation signal while being in a state of receiving the detection signal, the controlling unit may output a drive signal to drive one of the imaging unit and the table to the driving unit, in accordance with the operation signal.

Note 10:
The maneuvering unit may further include the judging unit.

The contact detecting parts may be configured to output a detection signal related to the contact detection to the judging unit.

When the detection signal is input, the judging unit may determine that it is possible to bring the one or both of the imaging unit and the table into operation.

When it is determined to be possible to bring the one or both of the imaging unit and the table into operation, the maneuvering unit may output an operation signal related to the operation of the handle unit to the controlling unit. The controlling unit may bring the one or both of the imaging unit and the table into operation according to the operation signal.

Note 11:
The plurality of contact detecting parts may include one or both of: a pressure sensor configured to detect pressure of the contact; and a temperature sensor configured to detect temperature of the contact.

The handle unit may be a joystick.

Note 12:
A display unit configured to display a medical image generated from an output of the imaging unit may further be provided.

On the basis of a result of the judgment, the display unit may display whether or not the handle unit is able to operate one of the imaging unit and the table.

Note 13:
The plurality of contact detecting parts may include two contact detecting parts positioned apart from each other and two contact detecting parts positioned adjacent to each other.

Note 14:
An X-ray diagnosis apparatus maneuvering device including:
a handle unit configured, while being gripped by an operator, to receive a maneuver to bring into operation one or both of: a table including a tabletop on which a patient is placed; and an imaging unit including an X-ray tube to radiate X-rays onto the patient and an X-ray detector to detect X-rays; and
a plurality of contact detecting parts provided for the handle unit and configured to detect contact made by the operator.

The plurality of contact detecting parts output a plurality of detection results obtained thereby, to an X-ray diagnosis apparatus including the table and the imaging unit.

What is claimed is:

1. An X-ray diagnosis apparatus comprising:
a table including a tabletop on which a patient is placed;
an imaging unit including an X-ray tube configured to radiate X-rays onto the patient and an X-ray detector configured to detect X-rays;
a maneuvering unit including a handle unit that is provided with a plurality of contact sensors to detect contact made by an operator and that is gripped by the operator and being configured to receive a maneuver to bring into operation one or both of the imaging unit and the table according to an operation of the handle unit; and
processing circuitry configured to judge whether or not one or both of the imaging unit and the table is to be brought into operation on a basis of a plurality of detection results obtained by the plurality of contact sensors and to bring the one or both of the imaging unit and the table into operation in accordance with a result of the judgment and the maneuver performed on the maneuvering unit.

2. The X-ray diagnosis apparatus according to claim 1, wherein
the imaging unit further includes a supporting arm configured to support the X-ray tube, with or without supporting the X-ray detector, and
in response to the maneuver performed on the handle unit accompanied by the contact detection, the processing circuitry implements at least one of the following operations: moving the supporting arm; changing an exterior shape of the supporting arm; and moving the tabletop.

3. The X-ray diagnosis apparatus according to claim 2, wherein
the moving of the supporting arm corresponds to at least one of: rotating of the supporting arm with respect to a rotation axis; sliding of the supporting arm; and translation of a supporting position in which the supporting arm is supported,
the changing of the exterior shape corresponds to at least one of: changing a distance between the X-ray tube and the X-ray detector; and rotating of the X-ray detector with respect to the X-ray tube, and
the moving of the tabletop corresponds to at least one of: translation along a vertical direction; sliding with respect to the table; and tilting of the tabletop with respect to a horizontal plane.

4. The X-ray diagnosis apparatus according to claim 1, wherein, when the handle unit has an operation while two contact sensors positioned apart from each other among the plurality of contact sensors are detecting the contact made by the operator, the processing circuitry outputs a drive signal to bring the one or both of the imaging unit and the table into operation, to an actuator configured to drive the one or both of the imaging unit and the table corresponding to the operation of the handle unit.

5. The X-ray diagnosis apparatus according to claim 4, wherein, when the handle unit has an operation while the two contact sensors are detecting no contact made by the operator, the processing circuitry does not output the drive signal to the actuator.

6. The X-ray diagnosis apparatus according to claim 1, wherein
the plurality of contact sensors include a first contact sensor and a second contact sensor, and
the second contact sensor is arranged in such a position where the contact detection is impossible when the operator comes into contact with the handle unit only from one direction to be in contact with the first contact sensor.

7. The X-ray diagnosis apparatus according to claim 1, wherein the plurality of contact sensors are arranged in at least two positions selected from among: a plurality of sections on one or more lateral faces of the handle unit and a tip end part of the handle unit.

8. The X-ray diagnosis apparatus according to claim 1, wherein the contact sensors are configured to output a detection signal related to the contact detection to the processing circuitry, the maneuvering unit is configured to output an operation signal related to the operation of the handle unit to the processing circuitry, and when having the operation signal input thereto while being in a state of receiving the detection signal, the processing circuitry determines that it is possible to bring the one or both of the imaging unit and the table into operation.

9. The X-ray diagnosis apparatus according to claim 8, further comprising: an actuator configured to drive the imaging unit and the table, wherein when having the operation signal input thereto while being in a state of receiving the detection signal, the processing circuitry outputs a drive signal to drive one of the imaging unit and the table to the actuator, in accordance with the operation signal.

10. The X-ray diagnosis apparatus according to claim 1, wherein the maneuvering unit further includes the processing circuitry, the contact sensors are configured to output a detection signal related to the contact detection to the processing circuitry, when the detection signal is input thereto, the processing circuitry determines that it is possible to bring the one or both of the imaging unit and the table into operation, when it is determined to be possible to bring the one or both of the imaging unit and the table into operation, the maneuvering unit outputs an operation signal related to the operation of the handle unit to the processing circuitry, and the processing circuitry brings the one or both of the imaging unit and the table into operation according to the operation signal.

11. The X-ray diagnosis apparatus according to claim 1, wherein the plurality of contact sensors include one or both of: a pressure sensor configured to detect pressure of the contact; and a temperature sensor configured to detect temperature of the contact, and the handle unit is a joystick.

12. The X-ray diagnosis apparatus according to claim 1, further comprising: a display device configured to display a medical image generated from an output of the imaging unit, wherein on a basis of a result of the judgment, the display device displays whether or not the handle unit is able to operate one of the imaging unit and the table.

13. The X-ray diagnosis apparatus according to claim 1, wherein the plurality of contact sensors include two contact sensors positioned apart from each other and two contact sensors positioned adjacent to each other.

14. An X-ray diagnosis apparatus maneuvering device comprising:

a handle unit configured, while being gripped by an operator, to receive a maneuver to bring into operation one or both of: a table including a tabletop on which a patient is placed; and an imaging unit including an X-ray tube to radiate X-rays onto the patient and an X-ray detector to detect X-rays; and a plurality of contact sensors provided for the handle unit and configured to detect contact made by the operator, wherein the plurality of contact sensors output a plurality of detection results obtained thereby, to an X-ray diagnosis apparatus including the table and the imaging unit.

\* \* \* \* \*